United States Patent [19]

Michejda et al.

[11] Patent Number: 5,508,289

[45] Date of Patent: Apr. 16, 1996

[54] BIS-ACRIDONE CHEMOTHERAPEUTIC DERIVATIVES

[75] Inventors: Christopher J. Michejda, North Potomac; Wieslaw M. Cholody, Frederick; Lidia Hernandez, Gaithersburg, all of Md.

[73] Assignee: The United States America as represented by the Department of Health and Human Services, Washington, D.C.

[21] Appl. No.: 213,315

[22] Filed: Mar. 14, 1994

[51] Int. Cl.$^6$ ............ A61K 31/435; A61K 31/41; C07D 487/02; C07D 471/00

[52] U.S. Cl. ............ 514/287; 514/288; 514/297; 546/64; 546/66; 546/103

[58] Field of Search ............ 546/64, 66, 103, 546/65, 79; 514/287, 288, 290, 284, 285, 297

[56] References Cited

U.S. PATENT DOCUMENTS 5,231,100   7/1993   Cholody et al. ............ 514/288

OTHER PUBLICATIONS

Canellakis, et al., "Diacridines: Bifunctional Intercalators, I. Chemistry, Physical, Chemistry and Growth Inhibitory Properties" *Biochimica et Biophysica Acta*, vol. 418, pp. 277–289 (1976).
Cholody, et al., "5–[Aminoalkyl)amino]imidazo[4,5,1-de] acridin–6–onesas a Novel Class of Antineoplastic Agents. Synthesis and Biological Activity", *Journal of Medicinal Chemistry*, vol. 33, No. 1, pp. 49–52 (1990).
Cholody, et al., "8–Substituted 5–[Aminoalkyl)amino] –6H–v–triazolo[4,5,1–deacridin–6–onesas Potential Antineoplastic Agents. Synthesis and Biological Activity", *Journal of Medical Chemistry*, vol. 33, No. 10, pp. 2852–2856 (1990).
Cholody, et al., "Chromophore–Modified Antineoplastic Imidazoacridinones. Synthesis and Activity against Murine Leukemias", *Journal of Medicinal Chemistry*, vol. 35, No. 2, pp. 378–382 (1992).
Capps, et al., "2–(Aminoalkyl)[5[nitropyrazolo[3,4,5–kl] acridines, a New Class of Anticancer Agents", *Journal of Medical Chemistry*, vol. 35, No. 26, pp. 4770–4778 (1989).
Chen, et al., "Diacridines, Bifunctional Intercalators. Chemistry and Antitumor Activity", *Journal of Medicinal Chemistry*, vol. 21, No. 9, pp. 868–874 (1978).
Gaugain, et al., "DNA Bifunctional Intercalators. 1. Synthesis and Conformational Properties of an Ethidium Homodimer and of an Acridine Ethidium Heterodimer", *Biochemistry*, vol. 17, No. 24, pp. 5071–5077 (1978).
Sinha, et al., "Synthesis and Antitumor Properties of Bis-(quinaldine) Derivatives", *Journal of Medicinal Chemistry*, vol. 20, No. 11 pp. 1528–1531 (1977).
Roques, et al., Preliminary Communication: "DNA Bifunctional Intercalators: Antileukemic Activity of New Pyridocarbazole Dimers", *Biochemical Pharmacology*, vol. 28, pp. 1811–1815 (1979).
Pelaprat, et al., "DNA Intercalating Compounds as Potential Antitumor Agents. 2. Preparation and Properties of 7 H–Pyridocarbazole Dimers", *Journal of Medicinal Chemistry*, vol. 23, No. 12 pp. 1336–1343 (1980).
Braa, et al., "Bis–naphthalimides: a new class of antitumor agents", *Anti–Cancer Drug Design*, vol. 8, pp. 257–268 (1993).

*Primary Examiner*—Gary L. Kunz
*Attorney, Agent, or Firm*—Morgan & Finnegan

[57] ABSTRACT

The present invention provides an anticancer compound having the structure:

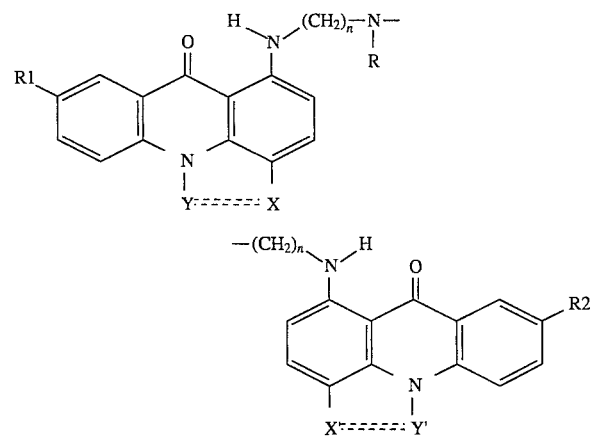

wherein R is —H, —CH$_3$, or —C$_2$H$_5$; R1 and R2 are independently —H, —OH, —NH$_2$, —OCH$_3$, —C(CH$_3$)$_3$, or a halogen atom; n is 2 to 6; X and X' are independently —N or —NO$_2$; Y and Y' are independently —N, —CH, or —H; and the double-slash represents a double bond or no bond; such that when X or X' is —N, Y or Y' is —CH or —N, and the double-slash is a double bond, and when X or X' is —NO$_2$, Y or Y' is —H, and the double-slash is no bond. The present invention also provides a pharmaceutical composition comprising the compound above and a pharmaceutically acceptable carrier.

28 Claims, 7 Drawing Sheets

FIG. 3B

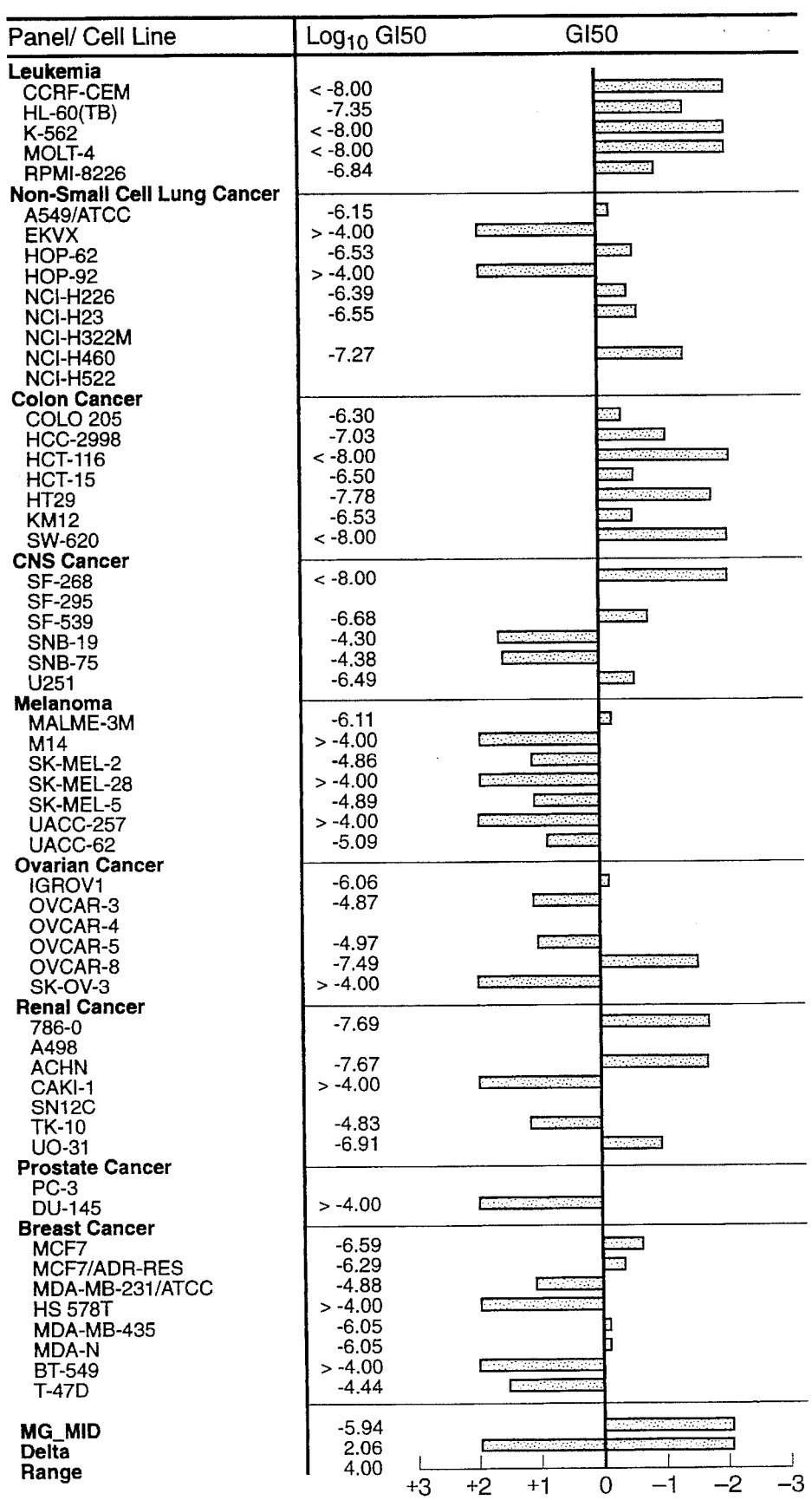

| Panel/ Cell Line | Log₁₀ GI50 |
|---|---|
| Leukemia | |
| CCRF-CEM | < -8.00 |
| HL-60(TB) | -7.35 |
| K-562 | < -8.00 |
| MOLT-4 | < -8.00 |
| RPMI-8226 | -6.84 |
| Non-Small Cell Lung Cancer | |
| A549/ATCC | -6.15 |
| EKVX | > -4.00 |
| HOP-62 | -6.53 |
| HOP-92 | > -4.00 |
| NCI-H226 | -6.39 |
| NCI-H23 | -6.55 |
| NCI-H322M | |
| NCI-H460 | -7.27 |
| NCI-H522 | |
| Colon Cancer | |
| COLO 205 | -6.30 |
| HCC-2998 | -7.03 |
| HCT-116 | < -8.00 |
| HCT-15 | -6.50 |
| HT29 | -7.78 |
| KM12 | -6.53 |
| SW-620 | < -8.00 |
| CNS Cancer | |
| SF-268 | < -8.00 |
| SF-295 | |
| SF-539 | -6.68 |
| SNB-19 | -4.30 |
| SNB-75 | -4.38 |
| U251 | -6.49 |
| Melanoma | |
| MALME-3M | -6.11 |
| M14 | > -4.00 |
| SK-MEL-2 | -4.86 |
| SK-MEL-28 | > -4.00 |
| SK-MEL-5 | -4.89 |
| UACC-257 | > -4.00 |
| UACC-62 | -5.09 |
| Ovarian Cancer | |
| IGROV1 | -6.06 |
| OVCAR-3 | -4.87 |
| OVCAR-4 | |
| OVCAR-5 | -4.97 |
| OVCAR-8 | -7.49 |
| SK-OV-3 | > -4.00 |
| Renal Cancer | |
| 786-0 | -7.69 |
| A498 | |
| ACHN | -7.67 |
| CAKI-1 | > -4.00 |
| SN12C | |
| TK-10 | -4.83 |
| UO-31 | -6.91 |
| Prostate Cancer | |
| PC-3 | |
| DU-145 | > -4.00 |
| Breast Cancer | |
| MCF7 | -6.59 |
| MCF7/ADR-RES | -6.29 |
| MDA-MB-231/ATCC | -4.88 |
| HS 578T | > -4.00 |
| MDA-MB-435 | -6.05 |
| MDA-N | -6.05 |
| BT-549 | > -4.00 |
| T-47D | -4.44 |
| MG_MID | -5.94 |
| Delta | 2.06 |
| Range | 4.00 |

FIG. 3D

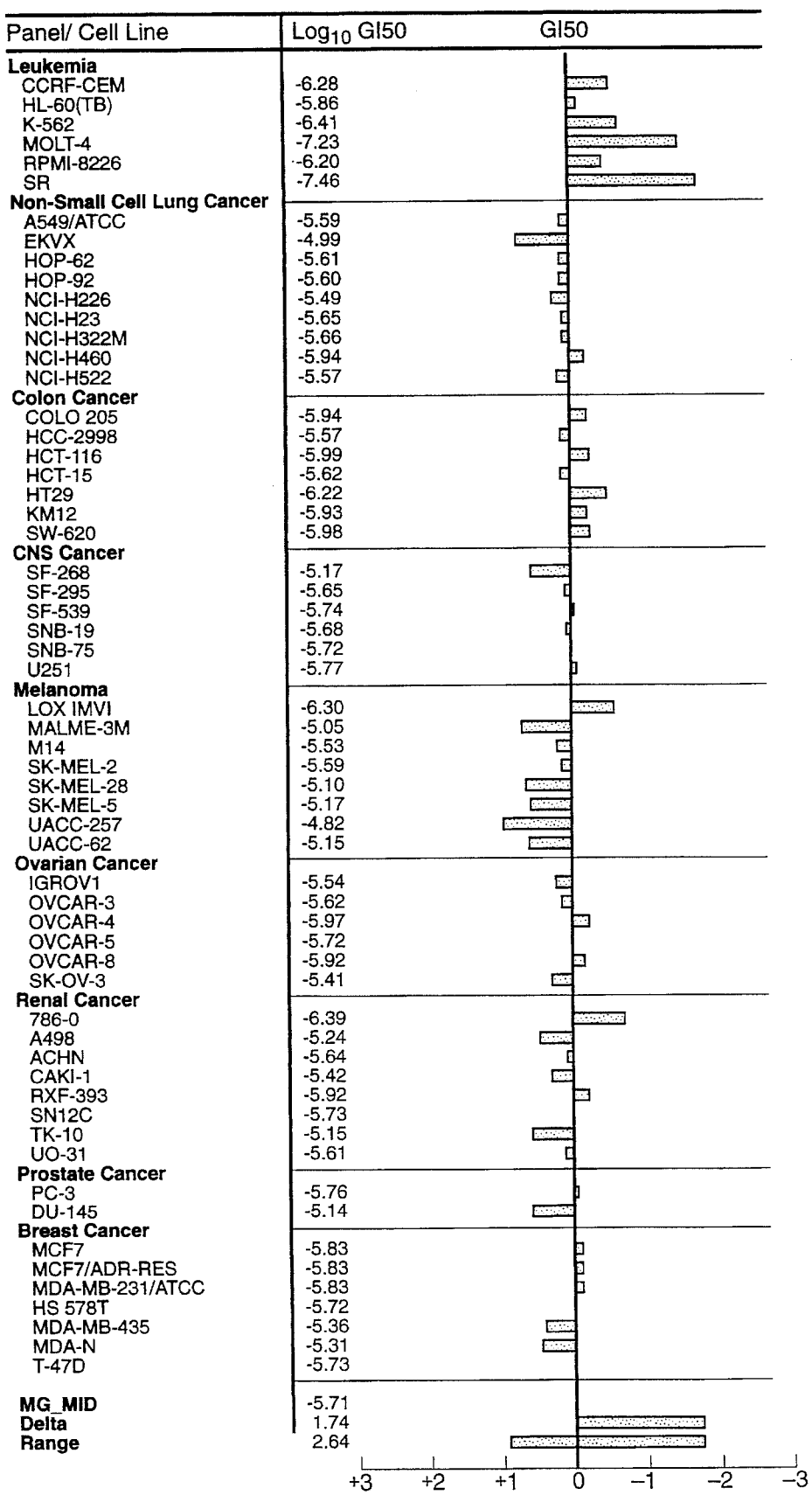

| Panel/ Cell Line | Log$_{10}$ GI50 |
|---|---|
| Leukemia | |
| CCRF-CEM | -6.28 |
| HL-60(TB) | -5.86 |
| K-562 | -6.41 |
| MOLT-4 | -7.23 |
| RPMI-8226 | -6.20 |
| SR | -7.46 |
| Non-Small Cell Lung Cancer | |
| A549/ATCC | -5.59 |
| EKVX | -4.99 |
| HOP-62 | -5.61 |
| HOP-92 | -5.60 |
| NCI-H226 | -5.49 |
| NCI-H23 | -5.65 |
| NCI-H322M | -5.66 |
| NCI-H460 | -5.94 |
| NCI-H522 | -5.57 |
| Colon Cancer | |
| COLO 205 | -5.94 |
| HCC-2998 | -5.57 |
| HCT-116 | -5.99 |
| HCT-15 | -5.62 |
| HT29 | -6.22 |
| KM12 | -5.93 |
| SW-620 | -5.98 |
| CNS Cancer | |
| SF-268 | -5.17 |
| SF-295 | -5.65 |
| SF-539 | -5.74 |
| SNB-19 | -5.68 |
| SNB-75 | -5.72 |
| U251 | -5.77 |
| Melanoma | |
| LOX IMVI | -6.30 |
| MALME-3M | -5.05 |
| M14 | -5.53 |
| SK-MEL-2 | -5.59 |
| SK-MEL-28 | -5.10 |
| SK-MEL-5 | -5.17 |
| UACC-257 | -4.82 |
| UACC-62 | -5.15 |
| Ovarian Cancer | |
| IGROV1 | -5.54 |
| OVCAR-3 | -5.62 |
| OVCAR-4 | -5.97 |
| OVCAR-5 | -5.72 |
| OVCAR-8 | -5.92 |
| SK-OV-3 | -5.41 |
| Renal Cancer | |
| 786-0 | -6.39 |
| A498 | -5.24 |
| ACHN | -5.64 |
| CAKI-1 | -5.42 |
| RXF-393 | -5.92 |
| SN12C | -5.73 |
| TK-10 | -5.15 |
| UO-31 | -5.61 |
| Prostate Cancer | |
| PC-3 | -5.76 |
| DU-145 | -5.14 |
| Breast Cancer | |
| MCF7 | -5.83 |
| MCF7/ADR-RES | -5.83 |
| MDA-MB-231/ATCC | -5.83 |
| HS 578T | -5.72 |
| MDA-MB-435 | -5.36 |
| MDA-N | -5.31 |
| T-47D | -5.73 |
| MG_MID | -5.71 |
| Delta | 1.74 |
| Range | 2.64 |

BIS-ACRIDONE CHEMOTHERAPEUTIC DERIVATIVES

BACKGROUND OF THE INVENTION

A number of acridine-based compounds which exhibit high antitumor activity recently have been reported. Cholody W. M., et al. (1990) described 5-[(Aminoalkyl)amino] imidazo[4,5,1-de]acridin-6-ones as a novel class of antineoplastic agents (J. Med. Chem. 33:49–52 (1990)). Cholody, W. M., et al. (1990) also described 8-substituted 5-[(aminoalkyl)amino]-6H-v-triazolo[ 4,5,1-de]acridin-6-ones as potential antineoplastic agents (J. Med. Chem. 33:2852–2856 (1990)). Cholody, W. M., et al. (1992) described the synthesis of chromophore modified antineoplastic imidazoacridinones and their activity against murine leukemias (J. Med. Chem. 35:378–382 (1992)). Capps, D. B., et al. described 2-(aminoalkyl)-5-nitropyrazolo[3,4,5-kl]acridines as a new class of anticancer agents (J. Med. Chem. 35:4770–4778 (1992)).

The compounds above have a tetracyclic planar chromophore bearing one side chain containing an (aminoalkyl)amino residue as a common structural feature. It is believed that DNA is the primary target for these compounds and they bind to DNA by intercalation.

Bifunctional compounds also have been studied as potential antitumor agents based upon the ability of acridines and other planar aromatic compounds to interact with DNA by intercalation. Chen, T. K., et al. (1978) studied diacridines as bifunctional intercalators (J. Med. Chem. 21:868–874 (1978)). Gaugain, B., et al. (1978) described the synthesis and conformational properties of an ethidium homodimer and an acridine ethidium heterodimer (Biochemistry 17:5071–5078 (1978)). Sinha, B. K., et al. (1977) described the synthesis and antitumor properties of bis(quinaldine) derivatives (J. Med. Chem. 20:1528–1531 (1977)). Roques, B. P., et al. (1979) described the antileukemic activity of pyridocarbazole dimers (Biochem. Pharmacol. 28:1811–1815 (1979)). Pelaprat, D., et al. (1980) described 7H-pyridocarbazole dimers as potential antitumor agents (J. Med. Chem. 23:1336–1343 (1980)). Brana, M. F., et al. (1993) described bis-naphthalimides as a class of antitumor agents (Anti-Cancer Drug Design 8:257–268 (1993)).

The rationale for the strong binding of bifunctional intercalators containing two aromatic rings systems joined by suitable linker to nucleic acids has been presented (Canellakis, E. S., et al. Biochim. Biophys. Acta 418:277–283 (1976)). It was found that although such compounds exhibit high affinity for DNA, this strong binding with DNA by intercalation is generally not related to antitumor activity.

Many factors, such as physicochemical characteristics of the planar chromophores, nature of the linking chain (its length, rigidity and ionization state), position of attachment, and other factors, strongly influence the binding with DNA and the biological action of these compounds. Additionally, it was found that there is no direct correlation between DNA-binding affinity and cytotoxicity.

Since structure-activity relationships in the group of bifunctional intercalators in relation to their in vivo antitumor action remain unclear, it is not possible to predict structures that will show such activity. Small structural modifications can drastically change biological properties of the agent. Accordingly, a goal exists to find other compounds with high antineoplastic activity, especially selectively directed towards specific tumors.

This invention relates to a novel class of acridine-based DNA bifunctional intercalators, and their use as antineoplastic agents. Since the compounds also emit a fluorescence when bound to DNA, they also may be used in assays for the detection of DNA.

SUMMARY OF THE INVENTION

The present invention provides a compound having the structure:

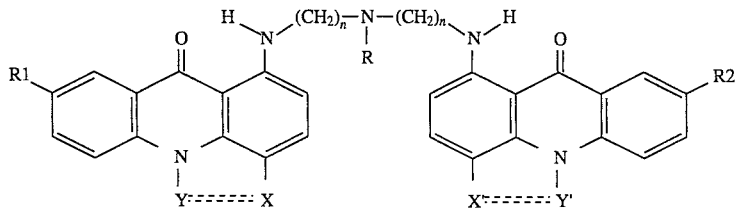

wherein R is —H, —CH$_3$, or —C$_2$H$_5$; R1 and R2 are independently —H, —OH, —NH$_2$, —OCH$_3$, —C(CH$_3$)$_3$, or a halogen atom; n is 2 to 6; X and X' are independently —N or —NO$_2$; Y and Y' are independently —N, —CH, or —H; and the double-slash represents a double bond or no bond; such that when X or X' is —N, Y or Y' is —CH or —N, and the double-slash is a double bond, and when X or X' is —NO$_2$, Y or Y' is —H, and the double-slash is no bond.

The present invention also provides a pharmaceutical composition comprising the compound above and a pharmaceutically acceptable carrier.

The present invention further provides a method for treating a neoplastic cell growth in a subject in need of such treatment which comprises administering to the subject an amount of the pharmaceutical composition above effective to treat the neoplastic cell growth.

Lastly, the present invention provides nucleic acid labeled with the compound above, and a method for detecting nucleic acid in a sample which comprises contacting the sample with the compound above under conditions permitting the compound to bind to the nucleic acid, detecting a fluorescent emission, thereby detecting the nucleic acid in the sample.

DETAILED DESCRIPTION OF THE INVENTION

Figure 1:
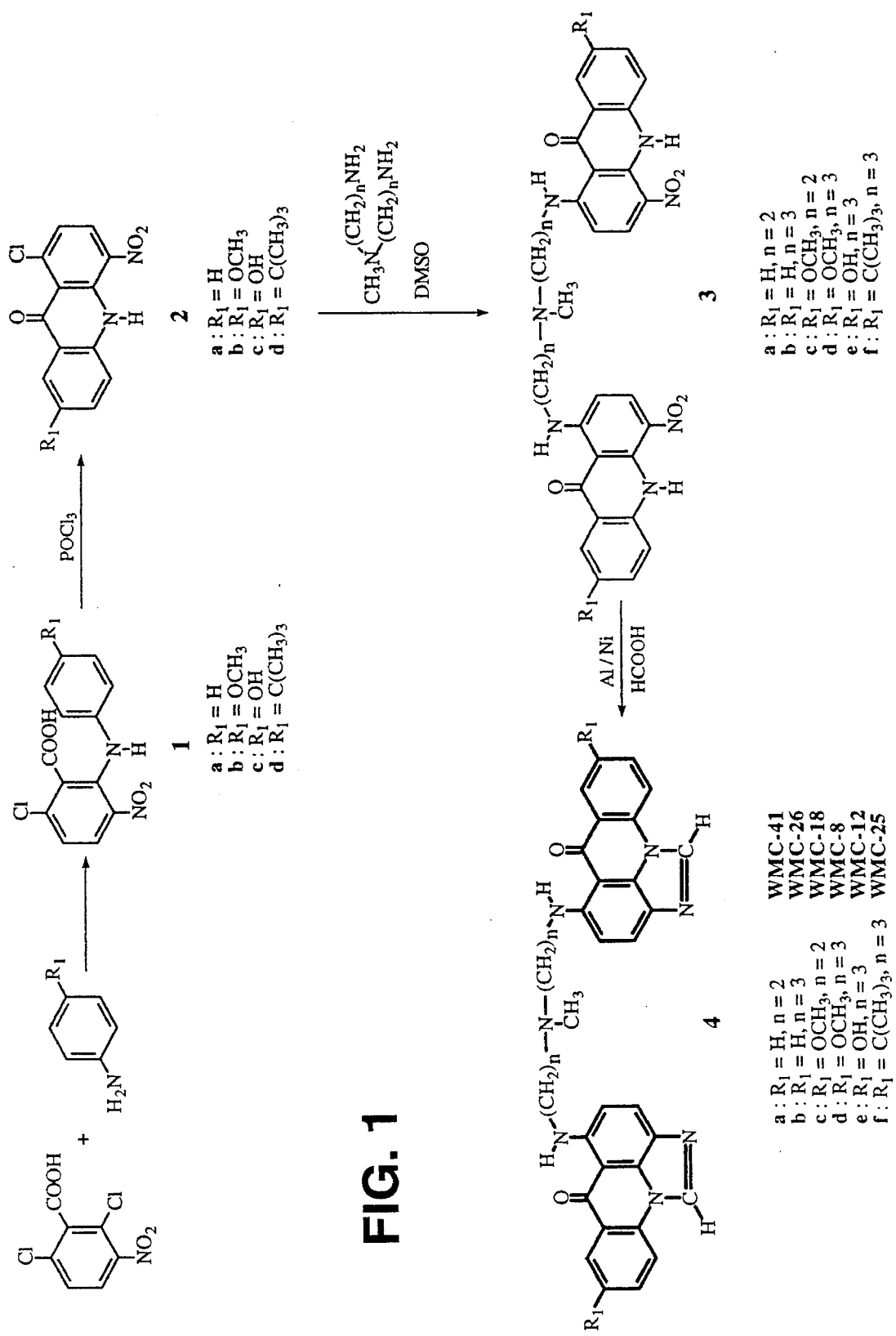
FIG. 1. Schematic diagram for the synthesis of symmetrical chromophore compounds.

The present invention provides a compound having the structure:

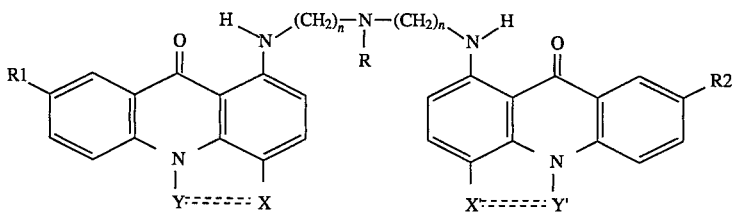

wherein R is —H, —$CH_3$, or —$C_2H_5$; R1 and R2 are independently —H, —OH, —$NH_2$, —$OCH_3$, —$C(CH_3)_3$, or a halogen atom; n is 2 to 6; X and X' are independently —N or —$NO_2$; Y and Y' are independently —N, —CH, or —H; and the double-slash represents a double bond or no bond; such that when X or X' is —N, Y or Y' is —CH or —N, and the double-slash is a double bond, and when X or X' is —$NO_2$, Y or Y' is —H, and the double-slash is no bond.

The compounds of the present invention may be present in the form of free bases or pharmaceutically acceptable acid addition salts thereof. Examples of suitable acids for salt formation are: methanesulfonic, sulfuric, hydrochloric, phosphoric, acetic, citric, lactic, ascorbic, maleic, and the like. In the preferred embodiment, the compounds of the present invention are present in the form of methansulfonates, such as trimethanesulfonate which can be hydrated to variable extents.

The present invention also provides a pharmaceutical composition comprising the compound above and a pharmaceutically acceptable carrier. The carrier must be "acceptable" in the sense of being compatible with the other ingredients of the formulation and not deleterious to the recipient thereof. The compound may be formulated with one or more pharmaceutically acceptable diluents or carriers, and optionally, any other ingredients which may be therapeutic per se, which are synergistic with the compound of the present invention. The concentration of the compound present in the formulation will depend upon the choice of carrier as well as the results desired.

Examples of suitable pharmaceutical carriers include lactose, sucrose, starch, talc, magnesium stearate, crystalline cellulose, methyl cellulose, carboxymethyl cellulose, glycerin, sodium alginate, gum arabic, powders, saline, water, among others. The choice of carrier will depend upon the route of administration. The formulations may conveniently be presented in unit dosage and may be prepared by methods well-known in the pharmaceutical art, by bringing the active compound into association with a carrier or diluent, as a suspension or solution, and optionally one or more accessory ingredients, e.g. buffers, flavoring agents, surface active agents, and the like.

For intravenous, intramuscular, subcutaneous, or intraperitoneal administration, the compound is combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For oral administration, the formulation may be presented as capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The present invention further provides a method for treating a neoplastic cell growth in a subject in need of such treatment which comprises administering to the subject an amount of the pharmaceutical composition above effective to treat the neoplastic cell growth.

The term "treatment" includes the partial or total inhibition of neoplastic cell growth, as well as the partial or total destruction of the neoplastic cells. The term "subject" includes a human or animal subject diagnosed as having cancer.

The administration may be affected by means known to those skilled in the art such as oral, rectal, topical intravenous, subcutaneous, intramuscular, or intraperitoneal routes of administration.

The dosage form and amount can be readily established by reference to known antineoplastic treatment or prophylactic regiments. In general, however, the dosage of the compound will be within the range of about 0.1 μg/kg to about 100 mg/kg. The actual dose will depend upon the route of administration, the pharmacokinetic properties of the individual treated, as well as the results desired.

Lastly, the present invention provides nucleic acid labeled with the compound above, and a method for detecting nucleic acid in a sample which comprises contacting the sample with the compound above under conditions permitting the compound to bind to the nucleic acid, detecting a fluorescent emission, thereby detecting the nucleic acid in the sample.

The nucleic acid may be either DNA or RNA, and is preferably DNA. The sample may be any sample which may contain nucleic acid. The fluorescent emission may be detected by means known to those skilled in the art, such as the use of a confocal microscope operating in the inverted mode.

The present invention is described in the following Experimental Details section, which sets forth specific examples to aid in an understanding of the invention, and should not be construed to limit in any way the invention as defined in the claims which follow thereafter.

EXPERIMENTAL DETAILS SECTION

Materials and Methods

All solvents used were reagent grade. All reagents were obtained either from Aldrich Chemicals or from Fluka and were used as received. Melting points were taken on an Electrothermal capillary melting points apparatus and are uncorrected. $^1$H NMR spectra were recorded on a Varian VXR-S spectrometer operating at 500 MHz. Chemical shifts are reported as $\partial$ units in ppm downfield from internal tetramethylsilane. NMR abbreviations used are as follows: br (broad), s (singlet), d (doublet), t (triplet), qu (quartet), qt (quintet), and m (multiplet). Coupling constants are given in Hz. Microanalytical results, indicated by atomic symbols, are within ±0.4% of the theoretical values.

Chemical Synthesis

The compounds of present invention in which both chromophores are identical were prepared by the route presented in FIG. 1. The intermediate chloronitroacridones 2a–d were prepared as described previously (Capps, D. B., et al. *J. Med. Chem.* 35:4770–4778 (1992); Lehmstedt, K., et al. *Chem. Berichte* 70:1526–1538 (1937)), or by procedures analogous thereto. The acridones were reacted with an equivalent amount of a suitable triamine to afford the bisnitroacridones 3, which were then reacted with formic acid and Raney alloy to give the final bisimidazoacridones 4.

Figure 2:
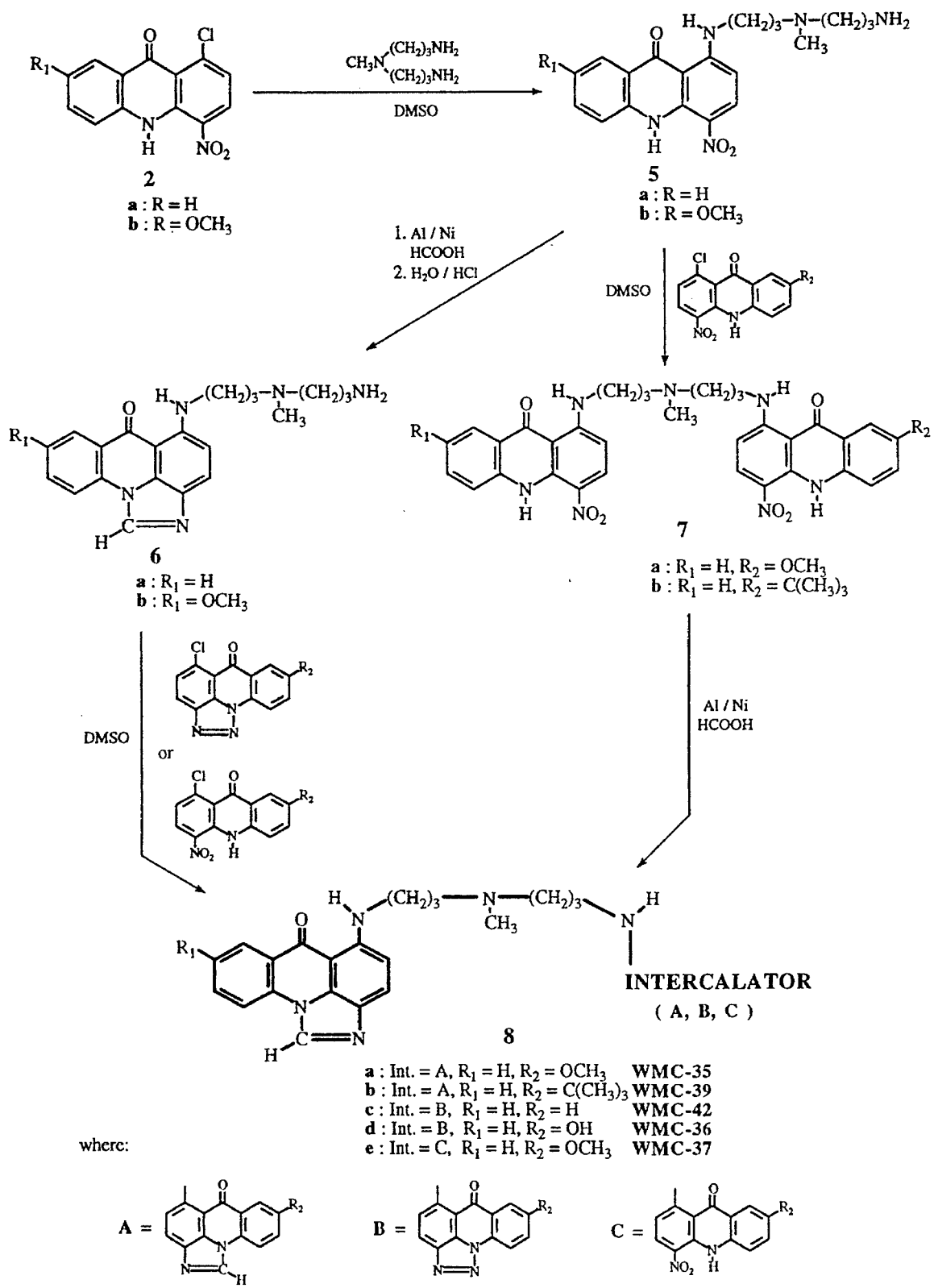
FIG. 2. Schematic diagram for the synthesis of unsymmetrical chromophore compounds.
Figure 3A:
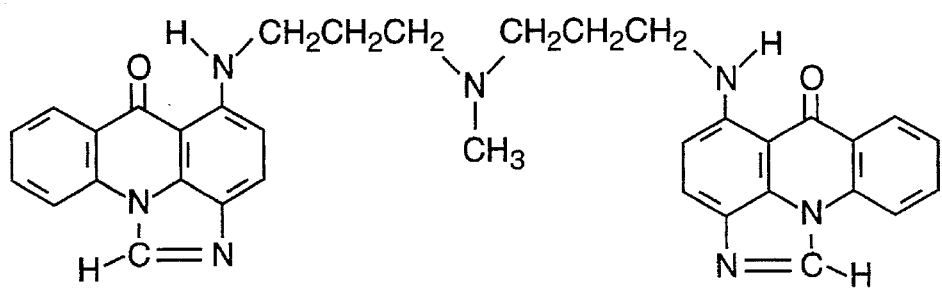
FIG. 3. A comparison of the cytotoxicity (GI$_{50}$) of compounds WMC-26 and WMC-8.
Figure 3C:
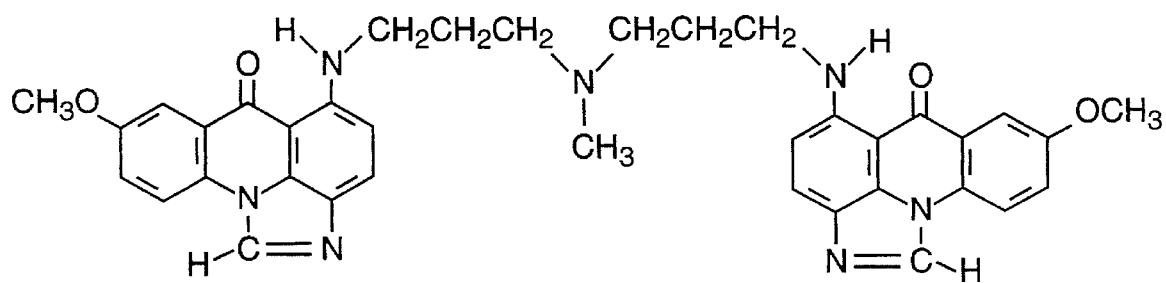

Unsymmetrical drugs were prepared according to FIG. 2. Chloronitroacridones 2 of FIG. 1 were reacted with an excess of triamine in such a way that the monosubstituted product 5 was formed. This material was transformed into the imidazoacridone derivative 6 or reacted with another chloronitroacridone to generate the unsymmetrical bisacridone 7. Compounds 6 were reacted with chlorotriazoloacridones, which were prepared according to the known methods (Cholody, W. M., et al. *J. Med. Chem.* 33:2852–2856 (1990)), to generate compounds 8 (where "intercalator" is B) or reacted with chloronitroacridone to generate derivative 8 (where "intercalator" is C). Treatment of 7 with formic acid and Raney alloy generated the unsymmetrical bisimidazoacridones 8 (where "intercalator" is A). The target compounds 4 and 8 were obtained as free bases which can be easily transformed into the addition salts described above by known procedures.

A detailed discussion of the synthesis of the compounds of the present invention is as follows.

Preparation of
2-[(4-tert-Butylphenyl)amino]-6-chloro-
3-nitrobenzoic acid (1d)

A mixture of 2,6-dichloro- 3-nitrobenzoic acid (4.72 g, 0.02 mol), 4-tertbutylaniline (4.47 g, 0.03 mol), lithium carbonate (1.48 g, 0.02 mol), and 1-propanol (10 mL) was refluxed with stirring for 20 h. The solvent was evaporated and to the residue, water (30 mL) and benzene (50 mL) were added. The mixture was made strongly basic with sodium hydroxide and stirred for 1h. Orange precipitate was collected by filtration and washed with benzene and ether. Dry precipitate was dissolved in water and acidified with diluted hydrochloric acid. Resulting precipitate was collected and crystallized from acetone-water to give 4.55 (65%) of the desired product, mp 201°–204° C. Anal. ($C_{31}H_{27}N_7O_6$) C, H, N.

Preparation of
7-tert-Butyl-1-chloro-4-nitro-9(1OH)-acridinone
(2d)

To a solution of 3a (3.485 g, 0.01 mol) in 1,2-dichloroethane (40 mL) POCl$_3$ (15 mL, 0.16 mol) was added and refluxed for 4.5 h. Solvents were removed under reduced pressure. To the residue, 40 mL of 1,4-dioxane - water mixture (8:1) was added, acidified with conc. hydrochloric acid and refluxed while stirring for 2 h. Water (100 mL) was added, the precipitate was collected by filtration and crystallized from N,N-dimethylformamide - water to give 3.106 g (94%) of the desired product, mp above 300° C. Anal. ($C_{31}H_{27}N_7O_6$) C, H, N.

General Procedure for the Preparation of
Bis(nitroacridones) (3)

Preparation of 2,2'-Bis [4-Nitro-9
(1OH)-acridinon-1
-ylaminol-N,N-diethylmethylamine (3a)

To a suspension of 1-chloro-4-nitro-9(1OH) -acridone (1.098 g, 0.004 mol) in dimethyl sulfoxide (20 mL), triethylamine (1 mL) and N$^2$-methyldiethylenetriamine (0.235 g, 0.002 mol) were added and stirred at 80° C. for 2 h. Water (200 mL) was added, made basic with sodium hydroxide water solution and stirred for 20 minutes. Precipitate was collected, washed with water and crystallized from N,N-dimethylformamide - water to afford 1.021 g (86%) of yellow 3a, mp 265°–267° C. Anal. ($C_{31}H_{27}N_7O_6$) C, H, N.

Preparation of 3,3'-Bis[7-Methoxy-4-nitro-9(1OH)
-acridinon-1-ylamino]-N-methyldipropylamine (3d)

To a suspension of 1-chloro-7-methoxy-4-nitro-9(1OH) -acridone (1.218 g, 0.004 mol) in dimethyl sulfoxide (20 mL), triethylamine (1 mL) and 3,3'-diamino-N-methyldipropylamine (0.305 g, 0.0021 mol) were added and stirred at 80° C. for 2 h. Water (200 mL) was added, made basic with sodium hydroxide water solution and stirred for 20 min. Precipitate was collected, washed with water and crystallized from N,N-dimethylformamide-water to give 1.20 g (93%) of yellow 3d, mp 256°–259° C. Anal. ($C_{35}H_{35}N_7O_8$) C, H, N. Compounds 3b, 3c,3e and 3f were obtained in an analogous manner.

3b: yield - 82%, mp 254°–256° C. Anal. ($C_{33}H_{31}N_7O_6$) C, H, N.

3c: yield - 88%, mp 268°–270° C. Anal. ($C_{33}H_{31}N_7O_8$) C, H, N.

3e: yield - 79%, mp 275°–278° C. Anal. ($C_{33}H_{31}N_7O_8$) C, H, N.

3f: yield - 74%, mp 199°–202° C. Anal. ($C_{41}H_{47}N_7O_6$) C, H, N.

General Procedure for the Preparation of Bis
(imidazoacridinones) (4)

A mixture of the bis(nitroacridinone) derivative (3a–f) (0.002 mol), 3.0 g of Raney alloy and 88% formic acid (30 mL) was refluxed with energetic stirring for 36 h. To the reaction mixture MeOH (100 mL) was added and the catalyst and inorganic salts were removed by filtration and washed with MeOH. Solvents were removed from the filtrate under reduced pressure. The residue was decolorized by heating with charcoal in 1% mixture of methanesulfonic acid in MeOH. The charcoal was removed by filtration. The filtrate was condensed and the product was precipitated by addition of acetone or ether. The precipitate was collected by filtration and recrystallized from MeOH-ether. Dry salt was dissolved in water and alkalized with sodium hydroxide (in the case of 4e with $NH_3$ aq.) to give precipitate of free base which was collected by filtration. The product was crystallized from suitable solvents mixture. Physical data for these compounds are presented in Table 1. Anal.:

4b: $^1$H NMR ($Me_2SO-d_6$) 8.98 (s, 2H, C1-H), 8.74 (t, 2H, Ar-NH-CH2-), 8.17 (dd, 2H, C7-H), 8.16 (d, 2H, C10-H), 7.71 (m, 2H, C9-H), 7.62 (d, 2H, J=8.9, C3-H), 7.36 (m, 2H, C8-H), 6.50 (d, 2H, J=8.9, C4-H), 3.36 (dt, 4H, —NH—$CH_2$—$CH_2$—), 2.55 (t, 4H, —$CH_2$—$CH_2$—$NCH_3$—), 2.28 (s, 3H, —$NCH_3$—), 1.90 (qt, 4H, —$CH_2$—$CH_2$—$CH_2$—).

4b·3 $CH_3SO_3H$: $^1$H NMR ($Me_2SO-d_6$) 9.36 (m, 1H, —$N^+HCLH_3$—), 9.32 (s, 2H, C1-H), 8.89 (br s, 2H, $N2^+$-H), 8.37 (d, 2H, C7-H), 8.32 (dd, 2H, C10-H), 7.99 (d, 2H, J=8.9, C3-H), 7.89 (m, 2H C9-H), 7.54 (m, 2H, C8-H), 6.88 (d, 2H, J=8.9 C4-H), 3.52 (t, 4H, —NH—$CH_2$—$CH_2$—), 3.33 (m, 2H, —NH—$CH_2$—$N^+HCH_3$—), 3.23 (m, 2H, —NH—$CH_2$—$N^+HCH_3$—), 2.86 (d, 3H, —$N^{+HCH}_3$—), 2.36 (s, 9H, $CH_3SO_3^-$), 2.10 (m, 4H, —$CH_2$—$CH_2$—$CH_2$—).

4d: $^1$H NMR ($Me_2SO-d_6$) 8.85 (s, 2H, C1-H), 8.69 (t, 2H, Ar—NH—CH2—), 8.00 (d, 2H, J=8.9, C10-H), 7.53 (d, 2H, J=3.0, C7-H), 7.53 (d, 2H, J=8.7, C3-H), 7.20 (dd, 2H, $J_m$=3.0, $J_o$=8.9, C9-H), 6.36 (d, 2H, J=8.7, C4-H), 3.79 (s, 6H, $CH_3O$-Ar), 3.38 (dt, 4H, —NH—$CH_2CH_2$—), 2.56 (t, 4H, —$CH_2$13 $CH_2$—$NCH_3$—), 2.28 (s, 3H, —$NCH_3$—), 191 (qt, 4H, —$CH_2$—CH2—$CH_2$—).

4d·3 $CH_3SO_3H$: $^1$H NMR ($Me_2SO-d_6$) 9.35 (m, 1H, —$N^+HCH_3$—), 9.26 (s, 2H, C1-H), 8.85 (br s, 2H, $N2^+$—H), 8.26 (d, 2H, J=9.0, C10-H), 7.94 (d, 2H, J=8.9, C3-H), 7.66 (d, 2H, J=3.0, C7-H), 7.44 (dd, 2H, $J_m$=3.0, $J_o$=8.9, C9-H), 6.82 (d, 2H, J=8.9, C9-H), 3.85 (s, 6H, $CH_3O$-Ar), 3.48 (t, 4H, —NH—$CH_2$—$CH_2$—), 3.34 (m, 2H, —NH—$CH_2$—$N^+HCH_3$—), 3.20 (m, 2 H, —$NHCH_2$—$N^+HCH_3$—), 2.87 (d, 3H, —$N^+HCH_3$—), 2.35 (s, 9H, $CH_3SO_3$—), 2.10 (m, 4H, —$CH_2$—$CH2CH_2$—).

4f: $^1$H NMR ($Me_2SO-d_6$) 8.99 (s, 2H, C1-H), 8.76 (t, 2H, Ar—NH—CH2—), 8.20 (d, 2H, J=2.4, C7-H), 8.12 (d, 2H, J=8.5, C10-H), 7.82 (dd, 2H, $J_m$=2.4, $J_o$8-5, C9-H), 7.62 (d, 2H, J=8.7, C3-H), 6.50 (d, 2H, J=8.7, C4-H), 3.36 (dt, 4H, —NH—$CH_2$—$CH_2$—), 2.54 (t, 4H, —$CH_2$—$CH_2$—$NCH_3$—), 2.27 (s, 3H, —$NCH_3$13 ), 1.89 (qt. 4H, $CH_2$—$CH_2$—$CH_2$—), 1.29 (s, 18H, $(CH_3)_3C$-Ar).

Preparation of
1-[3-[N-(3-Aminopropyl)methylamino]
propyl]amino-4-nitro-9(1OH)acridinone (5a)

To a suspension of 1-chloro-4-nitro-9(1OH)-acridone (2.747 g, 0.01 mol) in dimethyl sulfoxide (50 mL), 3,3'-diamino-N-methyldipropylamine (5.81 g, 0.04 mol) was added and stirred at room temperature for 2 h. Water (200 mL) was added and stirred for 10 min. The precipitate was collected by filtration and washed with water. Next, it was transferred into water (100 mL), acidified with hydrochloric acid and stirred for 15 min. Undissolved material was separated by filtration. The solution was made basic with sodium hydroxide and the product was extracted with chloroform. The extract was dried, solvent was evaporated and crude product was crystallized from benzene-hexane to give 3.1 g (81%) of yellow 5a, mp 109°–111° C. Anal. ($C_{20}H_{25}N_5O_3$) C, H, N. $^1$H NMR ($Me_2SO-d_6$) 11.86 (br s, 1H, N10-H), 8.36 (d, 1H, J=8.8, C3-H), 8.20 (dd, 1H, C8-H), 7.94 (d, 1H, C5-H), 7.77 (m, 1H, C6-H), 7.40 (m, 1H, C7-H), 6.58 (d, 1H, J=8.8, C2-H), 3.48 (t, 2H, —NH—$CH_2$—$CH_2$—) , 2.55 (m, 2H, —$CH_2$—$CH_2$—$NH_2$), 2.42 (t, 2H, —$CH_2$—$CH_2$—$NCH_3$—), 2.34 (t, 2H, —$NCH_3$—$CH_2$—$CH_2$—) , 2.16 (s, 3H, —$NCH_3$—) , 1.82 (qt, 2H, —$CH_2$—$CH_2$—$CH_2$—) , 1.50 (qt, 2H, —$CH_2$—$CH_2$ $CH_2$—).

Compound 5b was obtained in an analogous manner. Yield 82%, mp 140°–142° C. Anal. ($C_{21}H_{27}N_5O_4$) C, H, N.

Preparation of
5-[3-[N-(3-Aminopropyl)methylamino]
-propyl]amino-6H-imidazo[4,5,1-de]acridin-6-one
(6a)

A mixture of 5a (1.534 g, 0.004 mol), 3.0 g of Raney alloy and 96% formic acid (40 mL) was refluxed with energetic stirring for 24 h. To the reaction mixture MeOH (100 mL) was added and the catalyst and inorganic salts were removed by filtration and washed with MeOH. Solvents were removed from the filtrate under reduced pressure. To the residue 100 mL of MeOH - water (1:1) mixture and 3 mL of conc. hydrochloric acid were added and the solution was refluxed for 6 h. Solvents were evaporated under reduced pressure. The residue was dissolved in MeOH and acidified with hydrogen chloride. The product was precipitated by addition of acetone, collected by filtration and crystallized from MeOH - ether. Dry salt was dissolved in water and alkalized with sodium hydroxide to give oily precipitate of free base which was extracted with chloroform. The extract was dried, solvent was evaporated and product was crystallized from benzene - hexane to give 0.988 g (68%) of yellow 6a, mp 97°–99° C. Anal. ($C_{21}H_{25}N_5O$) C, H, N. $^1$H NMR ($Me_2SO-d_6$) 9.21 (s, 1H, C1-H), 8.91 (t, 1H, —NH—$CH_2$—), 8.42 (m, 1H, C7-H), 8.39 (m, 1H, C10-H), 8.00 (d, 1H, J=8.8, C3-H), 7.93 (m, 1H, C9-H) , 7.59 (m, 1H, C8-H), 6.85 (d, 1H, J=8.8, C4-H), 3.45 (t, 2H, —NH—$CH_2$—$CH_2$—), 2.61 (t, 2H, —$CH_2$—$CH_2$—$NH_2$), 2.43 (t, 2H, —$CH_2$—$CH_2$—$NCH_3$—) , 2.34 (t, 2H, —$NCH_3$—$CH_2$—$CH_2$—) , 2.17 (s, 3H, —$NCH_3$—) , 1.83 (qt, 2H, —$CH_2$—$CH_2$—CH2—) , 1.51 (qt, 2H, —$CH_2$—$CH_2$—$CH_2$—).

Preparation of
3-[7-Methoxy-4-nitro-9(1OH)-acridinon-1-ylamino]
-3'-[4-nitro-9(1OH) acridinon-1-ylamino]
-N-methyldipropylamine (7a)

A mixture of 5a (0.768 g, 0.002 mol) , 1-chloro-7-methoxy-4-nitro-9(1OH) acridinone (0.610 g, 0.002 mol), dimethyl sulfoxide (20 mL) and triethylamine (1 mL) was stirred at 70° C. for 4 h. To the reaction mixture water (200 mL) was added, alkalized with potassium hydroxide and stirred for 10 min. Precipitate was collected by filtration and washed with water. The crude product was crystallized from DMF-water to give 1.20 g (86%) of orange 7a, mp 192°–195° C. Anal. ($C_{34}H_{33}N_7O_7$) C, H, N. $^1$H NMR ($Me_2SO-d_6$) 12.15 (s, 1H, N10-H), 12.08 (s, 1H, N10-H), 11.73 (s, 1H, —NH—$CH_2$—), 11.61 (s, 1H, —NH—$CH_2$—), 8.11 (d, 1H), 8.01 (d, 1H), 7.55 (m, 3H), 7.24 (m, 1H), 7.19 (m, 1H), 7.09 (m, 1H), 6.27 (d,1H), 6.19 (d, 1H), 3.72 (s, 3H, —$OCH_3$), 3.37 (m, 4H), 2.55 (m, 4H), 2.25 (s, 3H, —NCH$_3$—), 1.88 (qt, 4H, CH$_2$—CH$_2$—CH$_2$—).

Preparation of 3-[6H-Imidazo[4,5,1-de]acridin-6-on-5-ylamino]-3'-[8-methoxy-6H-imidazo[4,5,1-de]acridin-6-on-5-ylamino]-N-methydipropylamine (8a).

This compound was prepared according to the general procedure for the preparation of the bisimidazoacridinones 4. Anal.: $^1$H NMR (Me$_2$SO-d$_6$): Unsubstituted chromophore 8.96 (s, 1H, C1-H), 8.75 (t, 1H, —NH—CH$_2$—), 8.17 (dd, 1H, C7-H), 8.16 (d, 1H, C10-H), 7.72 (m, 1H, C9-H), 7.67 (d, 1H, J=8.8, C3-H), 7.38 (m, 1H, C8-H), 6.51 (d, 1H, J=8.8, C4-H); 8-Methoxy chromophore 8.87 (s, 1H, C1-H), 8.66 (t, 1H, —NH—CH$_2$—), 8.00 (d, 1H, J=9.0, C10-H), 7.51 (d, 1H, J=3.0, C7-H), 7.46 (d, 1H, J=8.9, C3-H), 7.17 (dd, 1H, J$_m$=3.0, J$_o$=9-0, C9-H), 6.32 (d, 1H, J=8.9, C4-H), 3.75 (s, 3H, —OCH3); Aliphatic protons 3.35 (m, 2H, —NH—CH$_2$—CH$_2$—), 3.28 (m, 2H, —NH—CH$_2$—CH$_2$—), 2.55 (m, 4H, —CH$_2$—CH$_2$—NCH$_3$—), 2.28 (s, 3H, —NCH$_3$—), 1.90 (m, 4H, —CH$_2$—CH$_2$—CH$_2$—).

Preparation of 3-[8-Hydroxy-6H-v-triazolo[4,5,1-de]-acridin-6-on-5-ylamino]-3'-[6-H-imidazo[4,5,1-de]acridin-6-on-5-ylamino]-N-methydipropylamine (8d)

A mixture of 6a (0.364 g, 0.001 mol), 5-chloro-8-hydroxy-6-H-v-triazolo[4,5,1-de]acridin-6-one (0.272 g, 0.001 mol), dimethyl sulfoxide (8 mL) and triethylamine (1 mL) was stirred at 70° C. for 12 h. To the reaction mixture water (100 mL) was added, precipitate was collected by filtration and washed with water. The crude product was crystallized from DMF-water to give yellow 8d. Anal.: $^1$H NMR (Me$_2$SO-d$_6$): Imidazoacridone chromophore 8.93 (s, 1H, C1-H), 8.73 (t, 1H, —NH—CH$_2$—), 8.13 (dd, 1H, C7-H), 8.09 (d, 1H, C10-H), 7.66 (m, 1H, C9-H), 7.65 (d, 1H, J=8.8, C3-H), 7.31 (m, 1H, C8-H), 6.53 (d, 1H, J=8.8, C4-H); Triazoloacridone chromophore 10.17 (br s, 1H, C8-H), 9.18 (t, 1H, —NH—CH$_2$—), 8.07 (d, 1H, C10-H), 7.82 (d, 1H, J=9.2, C3-H), 7.55 (d, 1H, C7-H), 7.23 (dd, 1H, C9-H), 6.71 (d, 1H, J=9.2, C4-H); Aliphatic protons 3.45 (dt, 2H, —NH—CH$_2$—CH$_2$—), 3.36 (dt, 2H, —NH—CH$_2$—CH$_2$—), 2.55 (m, 4H, —CH$_2$—CH$_2$—NCH$_3$—), 2.29 (s, 3H, —NCH$_3$—), 1.90 (qt, 4H, —CH$_2$—CH$_2$—CH$_2$—).

Preparation of 3-[6H-Imidazo[4,5,1-de]acridin-6-on-5-ylamino]-3'-[7-methoxy-4-nitro-9(10H)-acridinon-1-ylamino]-N-methydipropylamine (8e)

This compound was prepared in the same manner as described for the preparation of 7a but 6a was used in place of 5a.

Colony Survival Assay

The human colon carcinoma cell line HCT-116 (Skehan, P., et al. J. Nat. Cancer Inst. 82:1107–1112 (1990)) was obtained from the American Type Culture Collection (Rockville, Md.). Cells were routinely cultured in Dulbecco's Minimum Essential Medium containing 10% Fetal Bovine Serum in a 5% CO$_2$ atmosphere, at 37° C. and in complete humidity.

Assays consisted of seeding single-cell suspensions at low density in 6-well culture dishes, and allowing them to attach and grow for 24 h. Compounds were then added at varying concentrations from stock solutions in DMSO, saline or water, and allowed to react in incubator for 1 h. Cells were then rinsed and fresh medium added; colonies were allowed to grow for 1 week with medium changes every 4 days. Wells were rinsed, cells fixed in methanol and stained with 1% Crystal Violet according to standard procedures.

Colonies containing greater than 30 cells were scored as survivors. Survivors were assessed as percentage of control colonies, which were those receiving only stock diluents but no compounds.

Results

Figure 4:
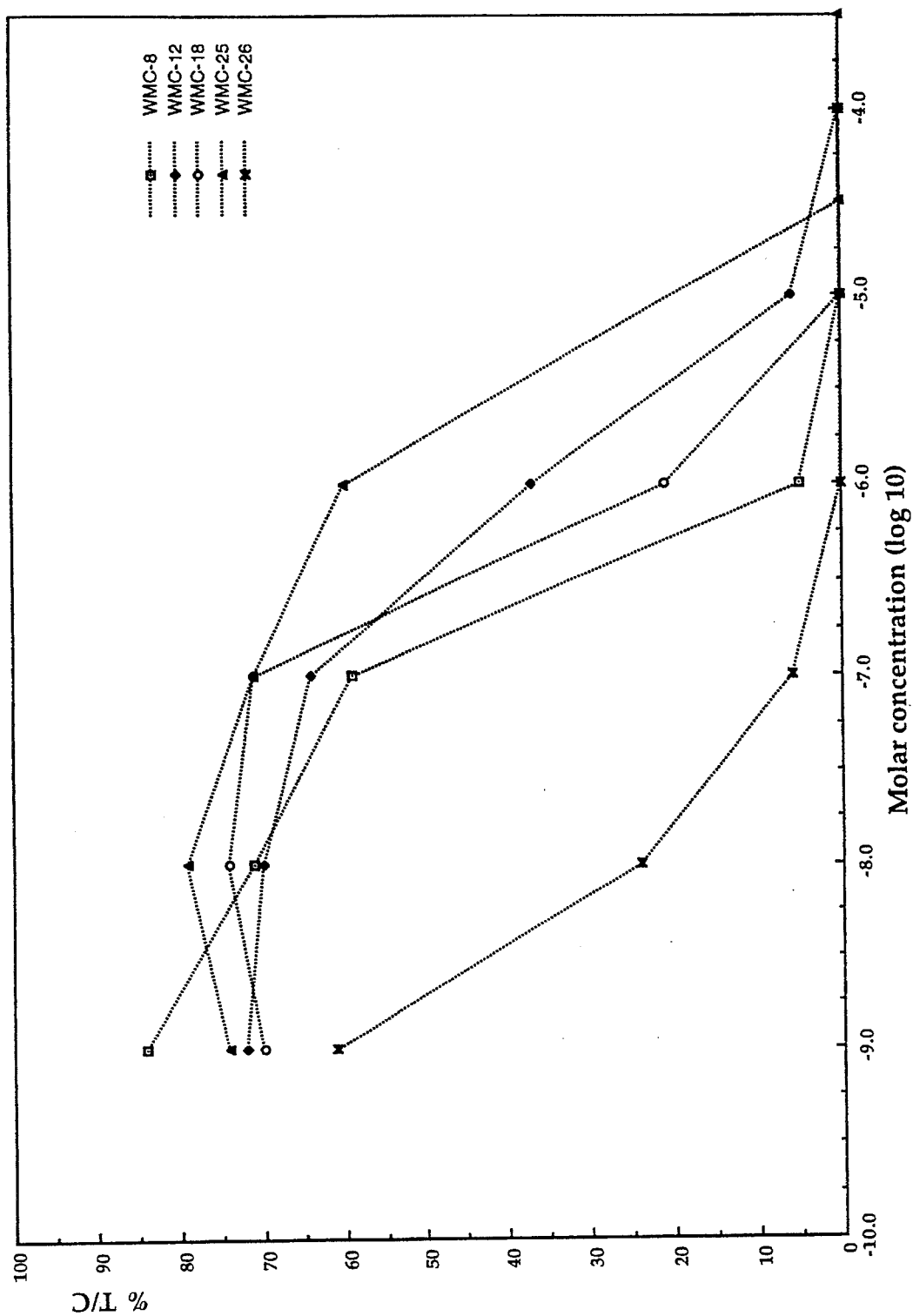
FIG. 4. A comparison of the cytotoxicity of compounds WMC-8 (□), WMC-12 (♦), WMC-18 (○), WMC-25 (▲), and WMC-26 (x) against colon adenocarcinoma HCT-116.
Figure 5:
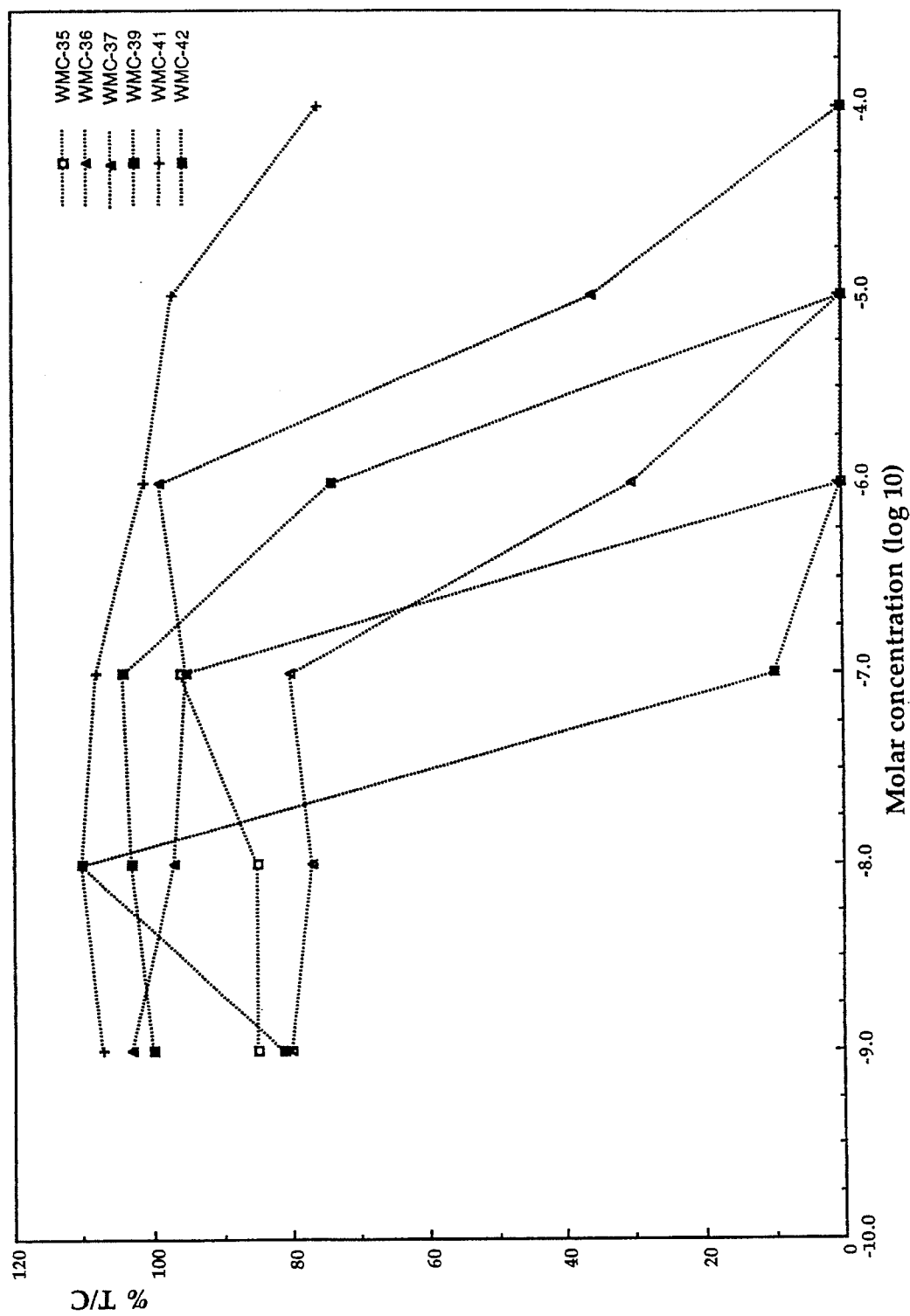
FIG. 5. A comparison of the cytotoxicity of compounds WMC-35 (□), WMC-36 (▲), WMC-37 (Δ), WMC-39 (■), WMC-41 (+), and WMC-42 (⊠) against colon adenocarcinoma HCT-116.

All the compounds of the present invention which have been tested (structures designated by the WMC numbers) showed strong antitumor activity both in vitro and in vivo. The standard NCI in vitro assay for cytotoxicity against 60 human tumor cell lines (Skehan, P., et al. J. Nat. Cancer Inst. 82:1107–1112 (1990); Boyd, M. R., et al. Principles Practice Oncol. 3: 1–12 (1989)) revealed that the compounds that contain at least one unsubstituted (R1=H) imidazoacridone ring system and linker that contains 6 methylene units exhibit significant selectivity towards colon tumor lines. FIG. 4 presents comparison of the GI$_{50}$ data for compounds WMC-26 in which both chromophores are unsubstituted (R$_1$=H) and its close dimethoxy (R$_1$=OCH$_3$) analog WMC-8. The selective toxicity against colon tumor, which is attributed to the unsubstituted chromophore, was confirmed in the in vitro colony survival assay on colon adenocarcinoma HCT-116 (see FIG. 4 and 5). Attention should be drawn to the extraordinary activity of compound WMC-26, whose T/C value for this tumor is in the nanomolar range. In spite of the high cytotoxicity of some of these compounds, the acute toxicity in nude mice was moderate. For example, compound WMC-26 was tolerated at a dose of 200 mg/kg per day, administered on three consecutive days, for a total dose of 600 mg/kg.

Almost all compounds of the present invention are highly fluorescent. When these compounds are added to live cells in culture there is a very rapid transfer of the fluorescence through the cytoplasm into the cell nucleus. This is best visualized using a confocal microscope operating in the inverted mode. The intense fluorescent staining of the nucleus of live cells suggest that the compounds could be used as vital stains for studying chromatin organization and behavior of DNA during cell cycle progression. Higher doses and longer exposure to compounds such as WMC-26 produced apoptotic morphology in the cellular nuclei. Thus these compounds could also be used in the study of chromatin organization during apoptosis.

All publications mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

TABLE 1

Physical Properties of Final Compounds

| Comp. | % yield | mp, °C. | recryst solv | formula |
|---|---|---|---|---|
| 4a | 58 | >300 | DMF-H$_2$O | C$_{33}$H$_{27}$N$_7$O$_2$ |
| 4b | 70 | 253–254 | DMF-H$_2$O | C$_{35}$H$_{31}$N$_7$O$_2$ |
| 4c | 67 | 275–277 | DMF-H$_2$O | C$_{35}$H$_{31}$N$_7$O$_4$ |
| 4d | 71 | 252–254 | DMF-H$_2$O | C$_{37}$H$_{35}$N$_7$O$_4$ |
| 4e | 59 | 297–300 | DMF-H$_2$O | C$_{35}$H$_{31}$N$_7$O$_4$ |

TABLE 1-continued

Physical Properties of Final Compounds

| Comp. | % yield | mp, °C. | recryst solv | formula |
|---|---|---|---|---|
| 4f | 61 | 150–152 | CHCl$_3$-hexane | C$_{43}$H$_{47}$N$_7$O$_2$ |
| 8a | 60 | 216–219 | DMF-H$_2$O | C$_{36}$H$_{33}$N$_7$O$_3$ |
| 8b | 51 | 153–156 | CH$_2$CL$_2$-hexane | C$_{39}$H$_{39}$N$_7$O$_2$ |
| 8c | 59 | 205–208 | benzene-hexane | C$_{34}$H$_{30}$N$_8$O$_2$ |
| 8d | 57 | 233–235 | DMF-H$_2$O | C$_{34}$H$_{30}$N$_8$O$_3$ |
| 8e | 73 | 237–239 | DMF-H$_2$O | C$_{35}$H$_{33}$N$_7$O$_5$ |

What is claimed is:

1. A compound having the structure:

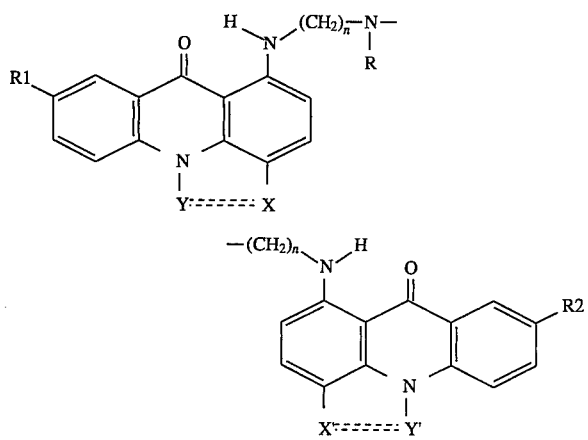

wherein R is —H, —CH$_3$, or —C$_2$H$_5$; R1 and R2 are independently —H, —OH, —NH$_2$, —OCH$_3$, —C(CH$_3$)$_3$, or a halogen atom; n is 2 to 6; X and X' are independently —N or —NO$_2$; Y and Y' are independently —N, —CH, or —H; and the double-slash represents a double bond or no bond; such that when X or X' is —N, Y or Y' is —CH or —N, and the double-slash is a double bond, and when X or X' is —NO$_2$, Y or Y' is —H, and the double-slash is no bond.

2. The compound of claim 1, wherein X and X' are —N, Y and Y' are —CH, and R is —CH$_3$.

3. The compound of claim 2, wherein R1 and R2 are —H, and n is 3.

4. The compound of claim 2, wherein R1 and R2 are —H, and n is 2.

5. The compound of claim 2, wherein R1 and R2 are —OCH$_3$, and n is 3.

6. The compound of claim 2, wherein R1 and R2 are —OCH$_3$, and n is 2.

7. The compound of claim 2, wherein R1 and R2 are —OH, and n is 3.

8. The compound of claim 2, wherein R1 and R2 are —C(CH$_3$)$_3$, and n is 3.

9. The compound of claim 2, wherein R1 is —H, R2 is —OCH$_3$, and n is 3.

10. The compound of claim 2, wherein R1 is —H, R2 is —C(CH$_3$)$_3$, and n is 3.

11. The compound of claim 1, wherein X is —N, Y is —CH, X' is —N, Y' is —N, R is —CH$_3$, and n is 3.

12. The compound of claim 11, wherein R1 is —H, and R2 is —H.

13. The compound of claim 11, wherein R1 is —H, and R2 is —OH.

14. The compound of claim 1, wherein X is —N, Y is —CH, X' is —NO$_2$, Y' is —H, R is —CH$_3$, R1 is —H, R2 is —OCH$_3$, and n is 3.

15. A pharmaceutical composition comprising the compound of claim 1 and a pharmaceutically acceptable carrier.

16. A pharmaceutical composition comprising the compound of claim 2 and a pharmaceutically acceptable carrier.

17. A pharmaceutical composition comprising the compound of claim 3 and a pharmaceutically acceptable carrier.

18. A pharmaceutical composition comprising the compound of claim 4 and a pharmaceutically acceptable carrier.

19. A pharmaceutical composition comprising the compound of claim 5 and a pharmaceutically acceptable carrier.

20. A pharmaceutical composition comprising the compound of claim 6 and a pharmaceutically acceptable carrier.

21. A pharmaceutical composition comprising the compound of claim 7 and a pharmaceutically acceptable carrier.

22. A pharmaceutical composition comprising the compound of claim 8 and a pharmaceutically acceptable carrier.

23. A pharmaceutical composition comprising the compound of claim 9 and a pharmaceutically acceptable carrier.

24. A pharmaceutical composition comprising the compound of claim 10 and a pharmaceutically acceptable carrier.

25. A pharmaceutical composition comprising the compound of claim 11 and a pharmaceutically acceptable carrier.

26. A pharmaceutical composition comprising the compound of claim 12 and a pharmaceutically acceptable carrier.

27. A pharmaceutical composition comprising the compound of claim 13 and a pharmaceutically acceptable carrier.

28. A pharmaceutical composition comprising the compound of claim 14 and a pharmaceutically acceptable carrier.

* * * * *